United States Patent [19]

Fengler et al.

[11] Patent Number: 4,548,934
[45] Date of Patent: Oct. 22, 1985

[54] 4H-1,4-BENZOTHIAZINE DERIVATIVES

[75] Inventors: Gerd Fengler, Krefeld; Dieter Arlt, Cologne; Klaus Grohe, Odenthal; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 518,901

[22] Filed: Aug. 1, 1983

[30] Foreign Application Priority Data

Aug. 4, 1982 [DE] Fed. Rep. of Germany ....... 3229124
Aug. 4, 1982 [DE] Fed. Rep. of Germany ....... 3229125
Aug. 4, 1982 [DE] Fed. Rep. of Germany ....... 3229126

[51] Int. Cl.[4] .................... C07D 279/16; A61K 31/54
[52] U.S. Cl. ................................. 514/225; 544/51; 544/52

[58] Field of Search ...................... 544/51, 52, 35, 37, 544/38, 32; 424/246, 247; 514/225

[56] References Cited

U.S. PATENT DOCUMENTS 1,867,863  7/1932  Muth ..................................... 544/51
2,374,181  4/1945  Dickey et al. ........................ 544/51
3,711,478  1/1973  Irmscher et al. ..................... 544/51

Primary Examiner—John M. Ford
Attorney, Agent, or Firm—Sprung Horn Kramer & Woods

[57] ABSTRACT

The present invention relates to novel 4H-1,4-benzothiazine derivatives and a method for their synthesis. The invention also relates to the pharmaceutical use of said derivatives, in particular their use as anti-infective agents, as agents for promoting growth and for improving feed stuff utilization in animals, and as preservations.

10 Claims, No Drawings

4H-1,4-BENZOTHIAZINE DERIVATIVES

The present invention relates to 4H-1,4-benzothiazine derivatives, a process for their preparation, their use as medicaments and in particular their use as anti-infective agents, as agents for promoting growth and for improving feedstuff utilisation in animals, and as preservatives. It has been found that the new 4H-1,4-benzothiazine derivatives of the general formula (I)

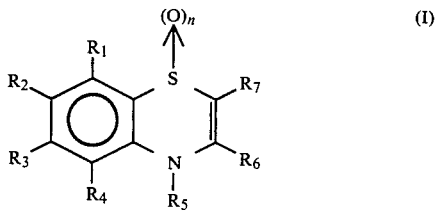

(I)

in which
n represents 0, 1 or 2,
$R_1$ and $R_4$ can be identical or different and denote hydrogen, optionally substituted alkyl or halogen,
$R_2$ and $R_3$ can be identical or different and represent hydrogen, optionally substituted alkyl, optionally substituted aryl, optionally substituted heterocyclyl, halogen, cyano, nitro, optionally substituted amino, alkoxy or alkoxycarbonyl.
$R_1$, $R_2$, $R_3$ and $R_4$ should not denote hydrogen simultaneously.
$R_5$ and $R_6$ can be identical or different and denote hydrogen, optionally substituted alkyl or optionally substituted cycloalkyl and $R_6$ furthermore represents alkoxycarbonyl and carboxyl and
$R_7$ represents hydrogen, optionally substituted alkyl, cyano, alkoxycarbonyl, carboxyl, alkylcarbonyl or arylcarbonyl,
and $R_6$ and $R_7$ can furthermore form an optionally substituted 5-membered or 6-membered carbocyclic structure.

Compounds of this general formula (I) possess powerful and broad antimicrobial activity and improve the growth and the feed utilisation in animals; they can be employed as anti-infective agents and as such have a broad spectrum of action.

The present invention furthermore relates to 4H-1,4-benzothiazine derivatives of the general formula (Ia)

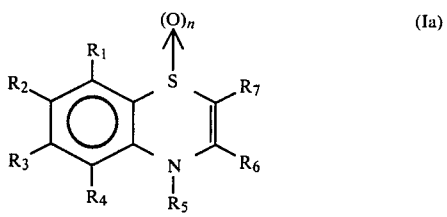

(Ia)

in which
n, $R_1$, $R_2$, $R_3$, $R_4$, $R_5$, $R_6$ and $R_7$ have the meaning given in the general formula (I), and $R_1$, $R_2$, $R_3$ and $R_4$ can also denote hydrogen simultaneously,
for use in combating disorders.

Furthermore, it has been found that the 4H-1,4-benzothiazine derivatives of the general formulae (I) and (Ia) are obtained if the open-chain compounds of the general formula (II)

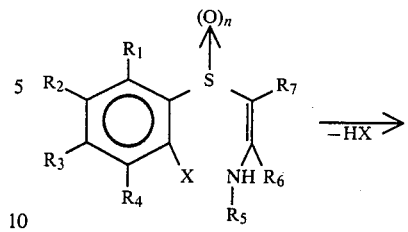

(II)

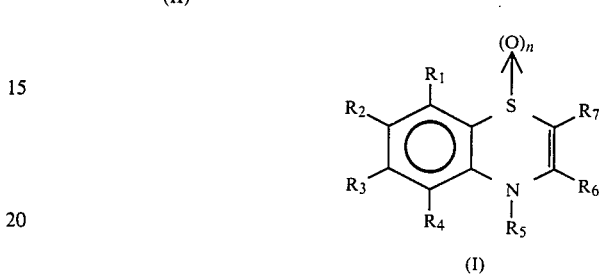

(I)

in which
n, $R_1$, $R_2$, $R_3$, $R_4$, $R_5$, $R_6$ and $R_7$ have the meaning given in the general formula (Ia), $R_6$ and/or $R_7$ not being intended to denote carboxyl, and X represents halogen, preferably chlorine or bromine,
are cyclised with bases in the presence of diluents.

Compounds of the general formula (Ia) in which $R_6$ and $R_7$ are carboxyl are readily obtainable by hydrolysis of the corresponding alkoxycarbonyl derivatives.

In the general formula (Ia), optionally substituted alkyl $R_1$, $R_2$, $R_3$, $R_4$, $R_5$, $R_6$ and $R_7$ represents straight-chain or branched alkyl having 1 to 4 carbon atoms. Optionally substituted methyl, ethyl, n- and i-propyl and n-, i- and t-butyl may be mentioned as examples.

Optionally substituted cycloalkyl $R_5$ and $R_6$ is monocyclic and contains 3 to 7, in particular 3 to 6, C atoms. Optionally substituted cyclopropyl, cyclobutyl, cyclopentyl and cyclohexyl may be mentioned as examples.

Optionally substituted aryl $R_2$ and $R_3$ is optionally substituted phenyl; substituents are in the o-, m- and p-positions.

Optionally substituted heterocyclyl $R_2$ and $R_3$ are heteroparaffinic, heteroaromatic or hetero-olefinic 5-membered to 7-membered, preferably 5-membered or 6-membered, rings having preferably 1 to 3, in particular 1 or 2, identical or different hetero atoms. Hetero atoms are oxygen, sulphur or nitrogen. Optionally substituted thienyl, furyl, oxazolyl, isoxazolyl, thiazolyl, isothiazolyl, pyrrolyl, imidazolyl, pyrazolyl, oxdiazolyl, thiadiazolyl, triazolyl, oxtriazolyl, thiatriazolyl, tetrazolyl, pyridyl, pyrazinyl, pyrimidinyl, tetrahydrofuranyl, dioxanyl, pyrrolidinyl, piperazinyl, piperidinyl, and morpholinyl may be mentioned as examples.

Optionally substituted amino $R_2$ and $R_3$ are mono- and dialkylamino.

Alkoxy preferably denotes methoxy and ethoxy.

Alkylcarbonyl $R_7$ represents methyl- and ethylcarbonyl, and arylcarbonyl $R_7$ represents optionally substituted phenylcarbonyl. Halogen denotes fluorine, chlorine, bromine and iodine, preferably fluorine, chlorine and bromine.

Optionally substituted alkyl, cycloalkyl, aryl and heterocyclyl radicals can carry one or more, preferably 1 to 3, in particular 1 or 2, identical or different radicals $R_8$, and $R_8$ represents straight-chain or branched alkyl having preferably 1 to 6, in particular 1 to 4 C atoms, for example methyl, ethyl, n- and i-propyl and n-, i- and t-butyl, and $CF_3$ and $CCl_3$, and represents aryl, for example phenyl, lower alkyl-oxy, preferably $CH_3O$— or $C_2H_5O$—, and represents aryloxy, for example phenoxy, and furthermore represents lower alkylthio, for example $CH_3S$— or $C_2H_5S$—, or represents HCO—NH—, or represents di-(lower alkylamino), for example dimethylamino or diethylamino, or represents lower alkyl-O—CO—, for example $CH_3O$—CO— and $C_2H_5O$—CO—, or represents halogen, preferably fluorine, chlorine or bromine, and —C≡N, COOH, —$NH_2$ and $NO_2$.

The 4H-1,4-benzothiazine derivatives according to the invention, of the general formulae (I) and (Ia), surprisingly exhibit powerful and broad antibacterial activity.

They have a very powerful general anti-infective action, particularly in combating bacterial infections.

The compounds defined by the general formulae (I) and (Ia) can be readily prepared by the process described above.

Some compounds defined by the general formula (I) can be prepared by the following processes:

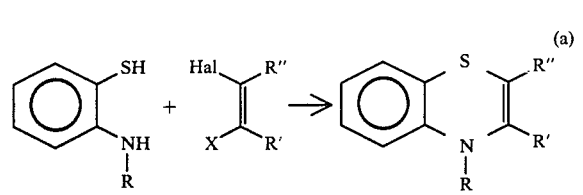
(a)

X=—OH, —NH aryl or halogen,
Hal=chlorine or bromine,
R=alkyl, R'=hydrogen or alkoxycarbonyl, R''=hydrogen, alkyl or alkoxycarbonyl

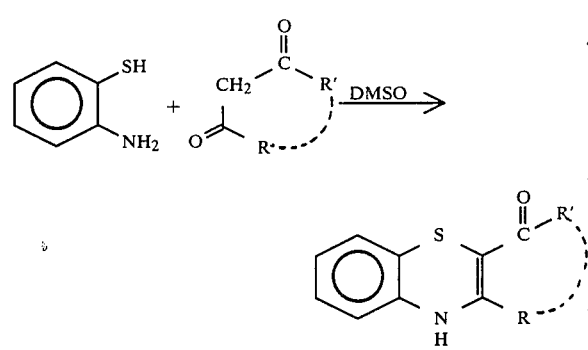

R=R'=alkyl, and R and R' form a 6-membered carbocyclic structure,

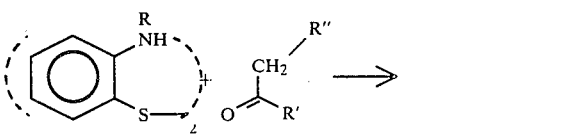

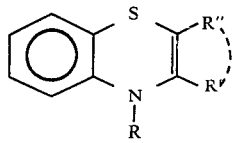

R=H or alkyl, R'=R''=alkyl, and R' and R'' form a 6-membered carbocylic structure

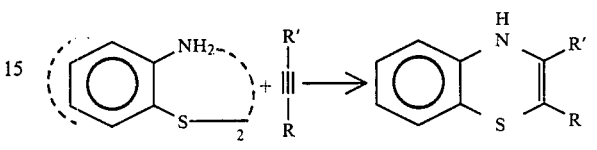

R=alkylcarbonyl or alkoxycarbonyl, and R'=H, phenyl or alkoxycarbonyl,

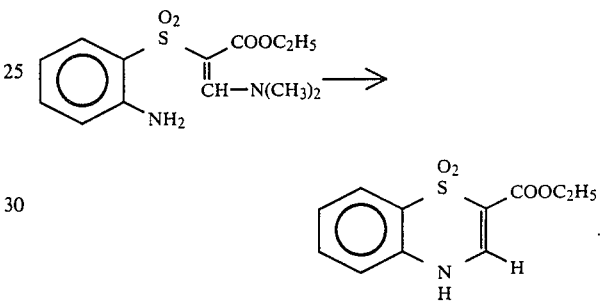

The methods (a) to (e) have the disadvantage that they do not permit synthesis of the desired 4H-1,4-benzothiazine derivatives—according to the general formula (I)—in in a technically satisfactory manner, since they require the use of specially substituted o-amino-thiophenols (a), (b) or of the corresponding disulphides (c), (d) or of o-nitrophenylsulphinates (e), which are technically very difficult to obtain and are therefore more expensive. In addition, the preparation of N-alkylated compounds frequently also requires an alkylating step. It was therefore the object of the invention to find a technically satisfactory synthesis which includes all patterns of substitution according to the general formula (1).

The object is achieved by the present invention, which is characterised in that the 4H-1,4-benzothiazine derivatives according to the invention, of the general formula (I), are obtained in a simple manner by cyclisation of the corresponding open-chain compounds of the general formula (V)

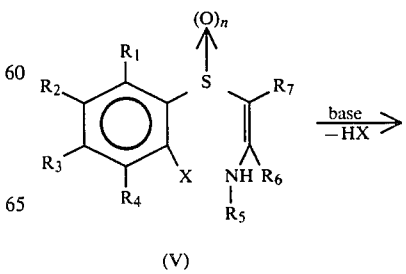

(V)

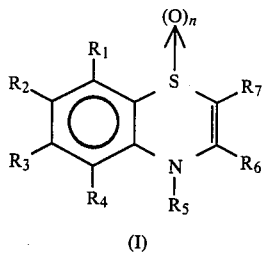

in the presence of a base and of diluents.

If, for example, ethyl α-[(2-chloro-5-nitrophenyl)sulphenyl]-β-ethylamino-acrylate (E/Z mixture) and potassium tert.-butylate are used as starting materials, the course of the reaction can be represented by the following equation:

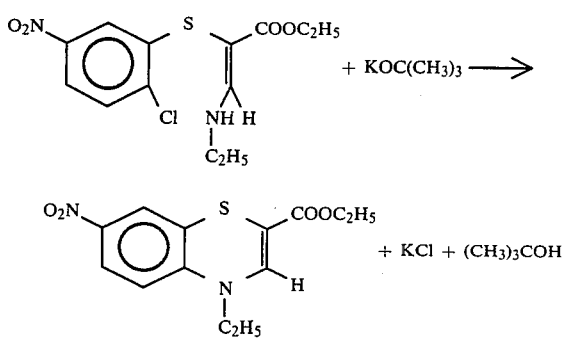

In the general formulae (I) and (V), optionally substituted alkyl $R_1$, $R_2$, $R_3$, $R_4$, $R_5$, $R_6$ and $R_7$ are straight-chain or branched alkyl radicals having 1 to 6, preferably 1 to 4, carbon atoms. Optionally substituted methyl, ethyl, n- and i-propyl and n-, i- and t-butyl may be mentioned as examples.

Optionally substituted cycloalkyl $R_5$ and $R_6$ is monocyclic and contains preferably 3 to 7, particularly preferably 3 to 5, C atoms. Optionally substituted cyclopropyl, cyclobutyl and cyclopentyl may be mentioned as examples.

Optionally substituted aryl $R_2$ and $R_3$ is optionally substituted phenyl. Substituents in the phenyl ring are in the o-, m- or p-position.

Optionally substituted heterocyclyl $R_2$ and $R_3$ are heteroparaffinic, heteroaromatic or hetero-olefinic 5-membered to 7-membered, preferably 5-membered or 6-membered, rings having preferably 1 to 3, particularly preferably 1 or 2, identical or different hetero atoms. Hetero atoms are oxygen, sulphur or nitrogen. Optionally substituted thienyl, furyl, oxazolyl, isooxazolyl, pyrazolyl, oxdiazolyl, thiadiazolyl, triazolyl, oxtriazolyl, thiatriazolyl, tetrazolyl, pyridyl, pyrazinyl, pyrimidinyl, tetrahydrofuranyl, dioxanyl, pyrrolidinyl, piperazinyl, piperidinyl and morpholinyl may be mentioned as examples.

Optionally substituted amino $R_2$ and $R_3$ are monoalkylamino and dialkylamino.

Alkoxy preferably denotes methoxy or ethoxy.

Halogen represents fluorine, chlorine, bromine and iodine, preferably fluorine, chlorine and bromine.

Alkylcarbonyl $R_7$ denotes straight-chain or branched alkylcarbonyl having preferably 1-4 C atoms, particularly preferably methyl- and ethylcarbonyl.

Arylcarbonyl $R_7$ represents optionally substituted phenylcarbonyl.

Optionally substituted alkyl, cycloalkyl, aryl and heterocyclyl radicals can carry one or more, preferably 1 to 3, in particular 1 or 2, identical or different radicals $R_8$, and $R_8$ represents straight-chain or branched alkyl having preferably 1 to 6, particularly preferably 1 to 4 C atoms, for example methyl, ethyl, n- and i-propyl and n-, i- and t-butyl, and $CF_3$ and $CCl_3$, and represents aryl, for example, phenyl, lower alkyloxy, preferably $CH_3O$— or $C_2H_5O$—, and represents aryloxy, for example phenoxy, and furthermore represents lower alkylthio, for example $CH_3S$— or $C_2H_5S$—, or represents HCO—NH—, or represents di-(lower alkylamino), for example dimethylamino or diethylamino, or represents lower alkyl—O—CO—, for example $CH_3O$—CO— and $C_2H_5O$—CO—, or represents halogen, preferably fluorine, chlorine or bromine, and —C≡N, COOH, —$NH_2$ and $NO_2$.

In the general formula (V), X represents halogen, preferably chlorine and bromine.

The derivatives to be employed according to the invention, of the formula (V) wherein n denotes 0, are obtained by reacting sulphenyl halides of the general formula (VI) with enamines of the general formula (VII) in the presence of an acid acceptor and of diluents.

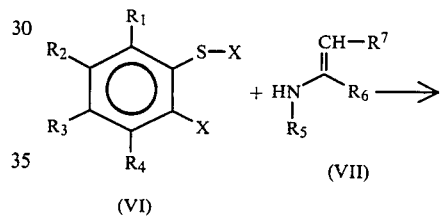

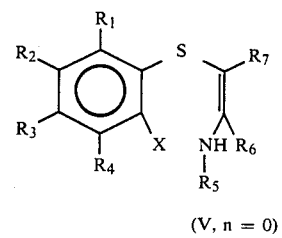

The compounds of the general formulae (VI) and (VII) in which $R_1$, $R_2$, $R_3$, $R_4$, $R_5$, $R_6$ and $R_7$ have meaning given above and X represents halogen are known from the literature or can be prepared by known processes (see for example: E. Kuhle, The Chemistry of the Sulfenic Acids, G. Thieme, Stuttgart 1973, and Organikum, VEB Deutscher Verlag der Wissenschaften, Berlin 1965, pages 371-372).

To prepare the starting materials of the formula (v, n=0), (VII) is advantageously initially introduced in the diluent which is also an acid acceptor, such as, for example, pyridine or triethylamine, and (VI) is added in an equimolar amount. The reaction temperature can be between 0° C. and 200° C., preferably between 20° C. and 100° C., and the reaction is carried out in general under atmospheric pressure. The reaction mixtures are worked up in a generally known manner in order to isolate (V, n=0).

The derivatives (V, n=0) are obtained as E/Z isomer mixtures, but both forms are suitable as a starting material for the process according to the invention.

The corresponding sulphoxides and sulphones of the formula (V, n=1 or 2) are obtained from (V, n=0) in a generally known manner by oxidation with suitable oxidising agents (see for example: C. Ferri, Reaktionen der organischen Synthese [Reactions of organic synthesis], C. Thieme Verlag, Stuttgart 1978, page 470).

Examples of bases which can be used in accordance with the invention are organometallic reagents, such as lithium diisopropylamide, butyl-lithium, phenyl-lithium or Grignard compounds, such as methyl magnesium iodide, or alkali metal alcoholates, such as potassium tert.-butylate, sodium methylate and sodium ethylate, as well as nitrogen bases, such as diazabicycloundecane and lutidine, and alkali metal carbonates.

Suitable diluents are all inert organic solvents. These preferably include ethers, such as dioxane and tetrahydrofuran, as well as dipolar aprotic solvents, such as dimethylsulphoxide, dimethylformamide and N-methylpyrrolidone. The process according to the invention can be carried out in the presence of only one solvent or of several solvents.

The reaction temperatures can be varied within a relatively wide range. In general, the reaction is carried out at between 0° C. and +250° C., preferably between 20° C. and 200° C.

The reaction can be carried out under atmospheric pressure as well as under reduced or elevated pressure. In general, the reaction is carried out under atmospheric pressure.

In carrying out the process according to the invention, the starting materials are employed in equimolar amounts.

To isolate the compounds according to the invention, the reaction mixtures are worked up in a generally known manner throughout.

The 4H-1,4-benzothiazine derivatives of the general formula (I) which can be prepared by the process according to the invention can be used as antibacterial agents and as lipoxygenase inhibitors, and they also represent valuable intermediate products for medicaments and plant protection agents.

If, for example, methyl α-[(2-chloro-5-nitrophenyl)-sulphenyl]-β-ethylamino-acrylate and potassium tert.-butylate are used as starting materials, the course of the reaction can be represented by the following equation:

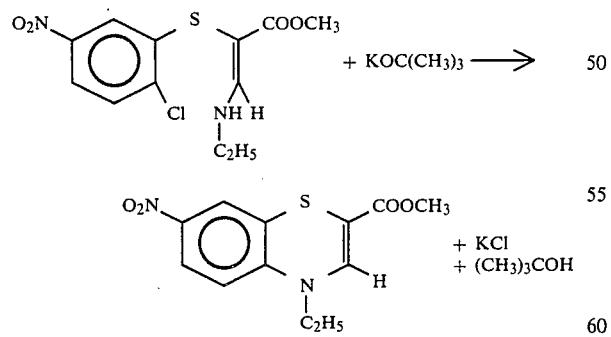

The compounds of the general formula (II, n=0) in which $R_1$, $R_2$, $R_3$, $R_4$, $R_5$, $R_6$ and $R_7$ have the meaning given in (Ia), except that $R_6$ and $R_7$ should not be carboxyl, and X represents halogen, preferably chlorine and bromine, are obtainable by reaction of sulphenyl halides of the formula (III) with enamines of the formula (IV)

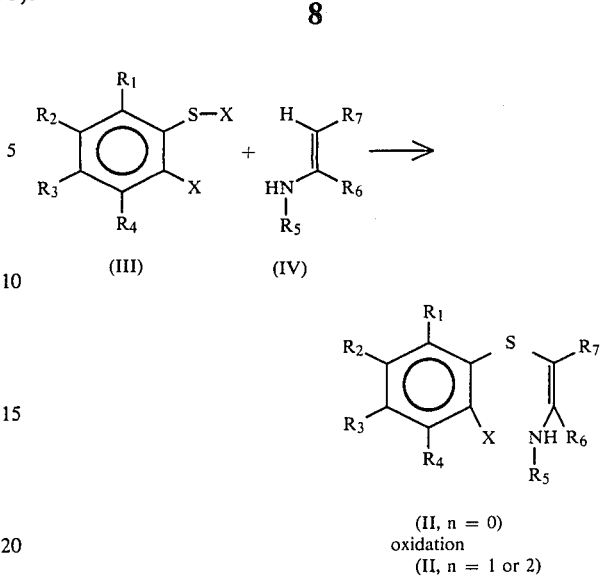

wherein $R_1$, $R_2$, $R_3$, $R_4$, $R_5$, $R_6$, $R_7$ and X have the meaning given above, in the presence of bases and, if appropriate, diluents. The compounds (II, n=1 or 2) can be obtained by oxidation of (II, n=0) with suitable oxidising agents in a generally customary manner (see C. Ferri, Reaktionen der organischen Synthese [Reactions of organic synthesis], G. Thieme Verlag, Stuttgart 1978, page 470).

Some of the derivatives (III) and (IV) are known, or they can be prepared by known processes (see E. Kühle, The Chemistry of the Sulfenic Acids, G. Thieme Verlag, Stuttgart 1973 and Organikum, VEB Deutscher Verlag der Wissenschaften, Berlin 1965, pages 371–372).

To prepare (II, N=0), the enamine of the formula (IV) is advantageously initially introduced in a diluent which is also a base, for example pyridine or triethylamine, and the sulphenyl halide is added in an equimolar amount. The reaction is carried out under atmospheric pressure, and the reaction temperatures can be varied within a relatively wide range. The reaction is carried out in general at between 0° C. and +200° C., preferably between 20° C. and 100° C.

To isolate the starting materials (II) for the process according to the invention, the reaction mixtures are worked up in a generally known manner throughout.

The derivatives (II) are obtained as E/Z isomer mixtures, but both forms are suitable as a starting material for the process according to the invention.

Examples of bases which can be used according to the invention are organometallic reagents, such as lithium diisopropylamide, butyl-lithium, phenyl-lithium or Grignard compounds, such as methyl magnesium iodide, or alkali metal alcoholates such as potassium tert.-butylate, sodium methylate and sodium ethylate, as wel as nitrogen bases, such as diazabicycloundecane and lutidine, and alkali metal carbonates.

Suitable diluents are all inert organic solvents. These preferably include ethers, such as dioxane and tetrahydrofuran, as well as dipolar aprotic solvents, such as dimethylsulphoxide, dimethylformamide and N-methylpyrrolidone. The process according to the invention can be carried out in the presence of only one solvent or of several solvents.

The reaction temperatures can be varied within a relatively wide range. In general, the reaction is carried out at between 0° C. and +250° C., preferably between 20° C. and 200° C.

The reaction can be carried out under atmospheric pressure as well as under reduced or elevated pressure. In general, the reaction is carried out under atmospheric pressure.

In carrying out the process according to the invention, the starting materials are employed in equimolar amounts.

To isolate the compounds according to the invention, the reaction mixtures are worked up in a generally known manner.

The compounds according to the invention exhibit a broad antibacterial spectrum against Gram-positive and Gram-negative germs, in particular against Enterobacteriaceae, which are resistant to other antibiotics or chemotherapeutic agents.

The compounds according to the invention exhibit powerful and broad antimicrobial activity coupled with low toxicity. These properties make it possible to use them as chemotherapeutic active compounds in medicine and as substances for preserving inorganic and organic materials, in particular organic materials of all kinds, for example polymers, lubricants, paints, fibres, leather, paper and timber, foodstuffs and water.

The active compounds according to the invention are active against a very broad spectrum of micro-organisms. With their aid Gram-negative and Gram-positive bacteria and bacteria-like micro-organisms can be combated and the illnesses caused by these pathogens can be prevented, alleviated and/or cured.

The compounds according to the invention are particularly active against bacteria and bacteria-like micro-organisms. They are therefore particularly suitable for the prophylaxis and chemotherapy, in human medicine and veterinary medicine, of local and systemic infections caused by these pathogens.

For example, local and/or systemic illnesses caused by the following pathogens or by mixtures of the following pathogens can be treated and/or prevented:

Micrococcaceae, such as Staphylococci, for example *Staphylococcus aureus* and *Staph. epidermis*, (Staph.=Staphylococcus); Lactobacteriaceae, such as Streptococci, for example *Streptococcus pyogenes*, α- or β-haemolysing Streptococci, non-(γ)-haemolysing Streptococci, Enterococci and *Dipolococcus pneumoniae* (Pneumococci) (Str.=Streptococcus); Enterobacteriaceae, such as Escherichiae bacteria of the coli group: Escherichia bacterial, for example *Escherichia coli*, Enterobacter bacteria, for example *E. aerogenes, E. cloacae,* Klebsiella bacteria, for example *K. pneumoniae*, Serratia, for example *Serratia marcescens* (E.=Enterobacter) (K.=Klebsiella), Proteae bacteria of the Proteus group: Proteus, for example *Proteus vulgaris, Pr. morganii, Pr. rettgeri* and *Pr. mirabilis*, (Pr.=Proteus); Pseudomonadaceae, such as Pseudomonas bacteria, for example *Pseudo-monas aeruginosa*, (Ps=Pseudomonas); Bacteroidaceae, such as Bacteroides bacteria, for example *Bacteroides fragilis*, (B.=Bacteroides).

The above list of pathogens is purely illustrative and is in no way to be interpreted as restrictive.

The following may be mentioned as examples of illnesses which can be prevented, alleviated and/or cured by the compounds according to the invention:

Illnesses of the respiratory passages and of the pharyngeal cavity; otitis; pharyngitis, pneumonia, peritonitis; pyelonephritis; cystitis; endocarditis; systemic infections; bronchitis, arthritis; and local infections.

The present invention also includes pharmaceutical formulations which, in addition to non-toxic, inert, pharmaceutically suitable excipients, contain one or more compounds according to the invention or which consist of one or more active compounds according to the invention, and processes for the preparation of these formulations.

The present invention also includes pharmaceutical formulations in dosage units. This means that the formulations are in the form of individual parts, for example tablets, dragees, capsules, pills, suppositories and ampoules, of which the content of active compound corresponds to a fraction or a multiple of an individual dose. The dosage units can contain, for example, 1, 2, 3 or 4 individual doses of $\frac{1}{2}$, $\frac{1}{3}$ or $\frac{1}{4}$ of an individual dose. An individual dose preferably contains the amount of active compound which is given in one administration and which usually corresponds to a whole, a half or a third or a quarter of a daily dose.

By non-toxic, inert pharmaceutically suitable excipients, there are to be understood solid, semi-solid or liquid diluents, fillers and formulation auxiliaries of all kinds.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds alongside the customary excipients such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium carbonate, (e) solution retarders, for example paraffin, and (f) resorption accelerators, for example quaternary ammonium compounds, (g) wetting agents, for example cetyl alcohol or glycerol monostearate, (h) adsorbents, for example kaolin and bentonite, and (i) lubricants, for example talc, calcium stearate and magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compound, optionally together with one or more of the abovementioned excipients, can also be in a micro-encapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid) or mixtures of these substances.

Ointments, pastes, creams and gels can contain in addition to the active compound or compounds the customary excipients, for example animal and vegetable fats, waxes, paraffins, starch, tragacanth, cellulose derivatives, polyethylene glycols, silicones, bentonites, silica, talc and zinc oxide or mixtures of these substances.

Powders and sprays can contain, in addition to the active compound or compounds, the customary excipients, for example lactose, talc, silica, aluminium hydroxide, calcium silicate and polyamide powders or mixtures of these substances. Sprays can additionally contain the customary propellants, for example chlorofluorohydrocarbons.

Solutions and emulsions can contain, in addition to the active compound or compounds, the customary excipients, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerol, glycerolformal, tetrahydrofurfuryl alcohol, polyethylene glycols and fatty acid esters of sorbitane, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol esters and sorbitane esters, microcrystalline cellulose, aluminium meta-hydroxide, bentonite, agar-agar and tragacanth or mixtures of these substances.

The formulation forms mentioned can also contain dyestuffs, preservatives and additives which improve the odour and flavour, for example peppermint oil and eucalyptus oil, and sweeteners, for example saccharin.

The therapeutically active compounds should preferably be present in the abovementioned pharmaceutical formulations in a concentration of about 0.1 to 99.5, preferably of 0.5 to 95, percent by weight of the total mixture.

The abovementioned pharmaceutical formulations can also contain other pharmaceutical active compounds in addition to the compounds according to the invention.

The abovementioned pharmaceutical formulations are prepared in a customary manner according to known methods, for example by mixing the active compound or compounds with the excipient or excipients.

The active compounds or the pharmaceutical formulations can be administered locally, orally, parenterally, intraperitoneally and/or rectally, preferably orally or parenterally, such as intravenously or intramuscularly.

In general it has proved advantageous both in human medicine and in veterinary medicine to administer the active compound or compounds according to the invention in total amounts of about 5 to about 1,000, preferably 10 to 200 mg/kg of body weight every 24 hours, optionally in the form of several individual administrations, in order to achieve the desired results. An individual administration contains the active compound or compounds according to the invention preferably in amounts of about 1 to about 250, especially of 3 to 60, mg/kg of body weight. However, it can be necessary to deviate from the dosages mentioned and in particular to do so as a function of the nature and body weight of the subject to be treated, the nature and the severity of the illness, the nature of the formulation and of the administration of the medicament, and the time or interval over which the administration takes place. Thus it can suffice in some cases to manage with less than the abovementioned amount of active compound whilst in other cases the abovementioned amount of active compound must be exceeded. The particular required optimum dosage and the type of administration of the active compounds can easily be determined by anyone skilled in the art, on the basis of his expert knowledge.

Where they are used as feedstuff additives, the new compounds can be administered in the customary concentrations and formulations, together with the feedstuff or with feedstuff formulations or with the drinking water. As a result, an infection caused by Gram-negative or Gram-positive bacteria can be prevented, alleviated and/or cured, and it is also possible to promote growth and to improve the utilisation of the feedstuff.

The new compounds are distinguished by powerful antibacterial actions which have been tested in vivo and in vitro, and by oral resorbability.

In order to extend the action spectrum and to increase the activity, compounds according to the invention can be combined with other antimicrobial active compounds, for example with penicillin, cephalosporins or other betalactams.

In order to extend the action spectrum and to increase the activity, the compounds according to the invention can also be combined with other antibiotics, for example aminoglycosides, such as, for example, gentamicin sisomicin, kanamicin, amikacin or tobramicin, tetracyclins or novobiocin.

The activity of the preparations according to the invention can be demonstrated, by way of example, by the following in vitro tests:

In vitro tests

The antibacterial action of the compounds of Examples 19, 20 and 21 were tested in the Agar dilution test. The concentration was 128 and 8 mcg per milliliter of agar.

Complete inhibition of growth was found for the following strains of bacteria (MIC; mcg/ml)

| Example No. | Staph 133 | Streptococ. W | Klebsiella 8085 |
|---|---|---|---|
| 19 |  | ≦128 |  |
|  |  | >8 |  |
| 20 | 128 | ≦128 | ≦128 |
|  | >8 | >8 | >8 |
| 21 |  | ≦128 |  |
|  |  | >8 |  |

The present invention furthermore relates to new substituted enamines, a process for their preparation and their use as intermediate products for the synthesis of 4H-1,4-benzothiazine derivatives which can be employed pharmacologically.

The new substituted enamines correspond to the general formula (VIII)

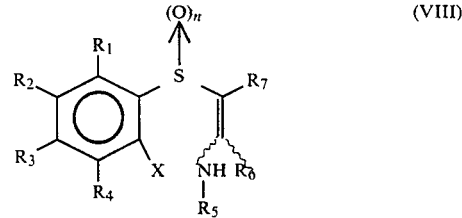

(VIII)

in which n represents 0, 1 or 2, $R_1$ and $R_4$ are identical or different and denote H, optionally substituted alkyl or halogen, $R_2$ and $R_3$ are identical or different and represent H, optionally substituted alkyl, optionally substituted aryl, optionally substituted heterocyclyl, halogen, optionally substituted amino, nitro, cyano, alkoxycarbonyl or alkoxy, $R_5$ and $R_6$ are identical or different and denote H, optionally substituted alkyl or optionally substituted cycloalkyl, and $R_7$ represents H, optionally substituted alkyl, cyano, alkoxycarbonyl, alkylcarbonyl or arylcarbonyl, and $R_6$ and $R_7$ can also form a 5-membered or 6-membered optionally substituted carbocylic structure, and X denotes halogen.

Substituted enamines of the formula (VIIIa)

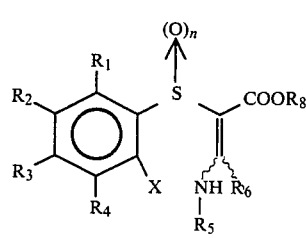

(VIIIa)

in which n, $R_1$, $R_2$, $R_3$, $R_4$, $R_5$, $R_6$ and X have the meaning given in formula (I) and $R_8$ represents optionally substituted alkyl, are particularly preferred.

The compounds according to the invention of the general formula (VIII) can occur as the E or Z isomer, and the present invention is therefore intended to relate to both forms and to the mixture.

In the general formula (VIII) and (VIIIa), optionally substituted alkyl $R_1$, $R_2$, $R_3$, $R_4$, $R_5$, $R_6$, $R_7$ and $R_8$ are straight-chained or branched alkyl radicals having up to 4 carbon atoms. Optionally substituted methyl, ethyl, n- and i-propyl and n-, i- and t-butyl may be mentioned as examples.

Optionally substituted cycloalkyl $R_5$ and $R_6$ is monocyclic and contains preferably 3 to 7, in particular 3 to 5, C atoms. Optionally substituted cyclopropyl, cyclobutyl and cyclopentyl may be mentioned as examples.

Optionally substituted aryl $R_2$ and $R_3$ is optionally substituted phenyl. Substituents in the phenyl ring are in the o-, m- or p-position.

Optionally substituted heterocyclyl $R_2$ and $R_3$ are heteroparaffinic, heteroaromatic or hetero-olefinic 5-membered to 7-membered, preferably 5-membered or 6-membered, rings having preferably 1 to 3, in particular 1 or 2, identical or different hetero atoms. Hetero atoms are oxygen, sulphur or nitrogen. Optionally substituted thienyl, furyl, oxazolyl, isoxazolyl, pyrazolyl, oxdiazolyl, thiadiazolyl, triazolyl, oxtriazolyl, thiatriazolyl, tetrazolyl, pyridyl, pyrazinyl, pyrimidinyl, tetrahydrofuranyl, dioxanyl, pyrrolidinyl, piperazinyl, piperidinyl and morpholinyl may be mentioned as examples.

Optionally substituted amino $R_2$ and $R_3$ are monoalkylamino and dialkylamino.

Alkoxy denotes methoxy or ethoxy.

Halogen represents fluorine, chlorine, bromine and iodine, preferably fluorine, chlorine and bromine.

Alkylcarbonyl $R_7$ denotes straight-chain or branched alkylcarbonyl having preferably 1-4 C atoms, in particular methyl carbonyl and ethylcarbonyl.

Arylcarbonyl $R_7$ represents optionally substituted phenylcarbonyl.

Optionally substituted alkyl, cycloalkyl, aryl and heterocyclyl radicals can carry one or more, preferably 1 to 3, in particular 1 or 2, identical or different radicals $R_8$, and $R_8$ represents straight-chain or branched alkyl having preferably 1 to 6, in particular 1 to 4 C atoms, for example methyl, ethyl, n- and i-propyl and n-, i- and t-butyl, and $CF_3$ and $CCl_3$, and represents aryl, for example phenyl, lower alkyl-oxy, preferably $CH_3O-$ or $C_2H_5O-$, and represents aryloxy, for example phenoxy, and furthermore represents lower alkylthio, for example $CH_3S-$ or $C_2H_5S-$, or represents $HCO-NH-$, or represents di-(lower alkylamino), for example dimethylamino or diethylamino, or represents lower alkyl-O—CO—, for example $CH_3O-CO-$ and $C_2H_5O-CO-$, or represents halogen, preferably fluorine, chlorine or bromine, and $-C\equiv N$, COOH, $-NH_2$ and $NO_2$.

The compounds according to the invention, of the general formula (VIII), for n=0, can be prepared by reacting sulphenyl halides of the formula (IX) with substances of the formula (X)

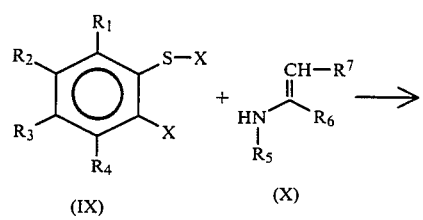

(IX)        (X)

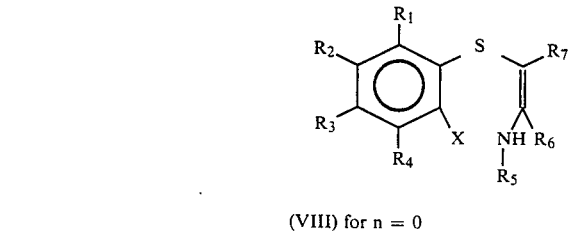

(VIII) for n = 0 wherein $R_1$, $R_2$, $R_3$, $R_4$, $R_5$, $R_6$, $R_7$ and X have the meaning given in the general formula (VIII)

in the presence of bases and, if appropriate, diluents.

The compounds of the general formulae (IX) and (X) are known from the literature or can be prepared by known processes (see for example: E. Kühle, The Chemistry of the Sulfenic Acids, G. Thieme, Stuttgart 1973, and Organikum, VEB Deutscher Verlag der Wissenschaften, Berlin 1965, pages 371-372).

If, for example, 2,4-dichloro-phenylsulphenyl chloride and methyl β-ethylamino-acrylate are used as starting materials, the course of the reaction can be represented by the following equation:

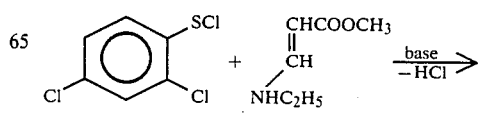

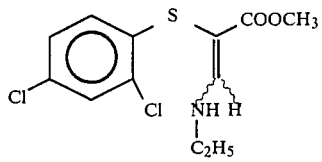

Suitable bases are inorganic and organic bases.

Sodium hydroxide, potassium hydroxide and calcium hydroxide, alkali metal carbonates and alkali metal bicarbonates may be mentioned as examples of inorganic bases. Examples of suitable organic bases are tertiary amines, preferably lower alkylamines, for example triethylamine, and/or cyclic bases, for example pyridine.

Suitable diluents are all inert organic solvents. These preferably include hydrocarbons, such as benzene and toluene, chlorinated hydrocarbons, such as methylene chloride, chloroform, carbon tetrachloride, 1,2-dichloroethane, 1,2,2-trichloroethane and chlorobenzene, as well as ethers, such as diethyl ether, dioxane or tetrahydrofuran. The process according to the invention can be carried out in the presence of only one organic solvent or of several organic solvents or water or one of more water-immiscible solvents.

Preferred diluents are those which are at the same time bases, for example pyridine or triethylamine.

The reaction temperatures can be varied within a relatively wide range. In general, the reaction is carried out at between about 0° C. and about 200° C., preferably between 20° C. and 100° C.

The reaction can be carried out under atmospheric pressure, but also under reduced or elevated pressure. In general, the reaction is carried out under atmospheric pressure.

In carrying out the process according to the invention, the reactants are preferably brought to reaction in equimolar amounts.

To isolate the compounds according to the invention, the reaction mixtures are worked up in a known manner.

The compounds according to the invention, of the general formula (VIII), for n=1 or 2 are obtained by oxidation of the substances (VIII), for n=0, with suitable oxidising agents.

If, for example, methyl α-[(2,4-dichlorophenyl)sulphenyl]-β-ethylamino-acrylate and m-chloroperbenzoic acid are used as starting materials, the course of the reaction can be represented by the following equation:

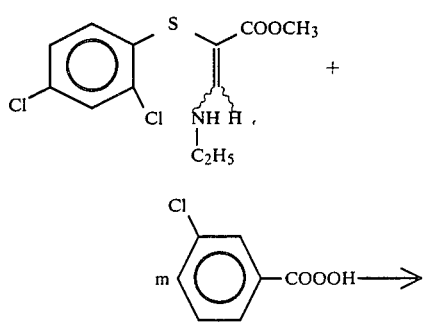

m = 1, 2

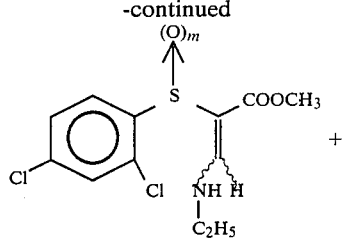

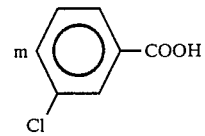

The oxidising agents which can be used according to the invention are likewise known, and hydrogen peroxide, performic acid, peracetic acid, perbonzoic acid, m-chloroperbenzoic acid, sodium metaperiodate and atmospheric oxygen may be mentioned as examples. Other suitable oxidising agents are described in C. Ferri, Reaktionen der organischen Synthese [Reactions of organic substances] (C. Thieme Verlag, Stuttgart 1978, page 470).

Suitable diluents are all inert organic solvents. These preferably include chlorinated hydrocarbons, such as methylene chloride, chloroform, carbon tetrachloride, 1,2-dichlorethane, 1,2,2-trichlorethane and chlorobenzene, alcohols, preferably methanol, ethanol and isopropanol, lower fatty acids, preferably formic acid, acetic acid and propionic acid and water. The process according to the invention can be carried out in the presence of only one solvent or of several solvents.

The reaction temperatures can be varied within a relatively wide range. In general, the reaction is carried out at between about −20° C. and about +100° C., preferably between 0° C. and +60° C. The reaction can be carried out at atmospheric pressure, but also under reduced or elevated pressure. In general the reaction is carried out under atmospheric pressure.

In carrying out the process according to the invention, the appropriate amount of oxidising agent in each case is employed for the preparation of the sulphoxides ((I), n=1) or of the sulphones ((VIII), n=2).

To isolate the compounds according to the invention, the reaction mixtures are worked up in a generally known manner throughout.

The derivatives according to the invention, of the formula (VIII) are important intermediate products for the synthesis of 4H-1,4-benzothiazine derivatives which can be employed pharmacologically.

EXAMPLE 1

Preparation of methyl α-[(pentachlorophenyl)-sulphenyl]-β-ethylamino-acrylate

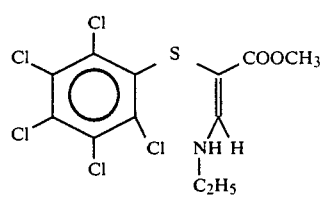

0.1 mol of methyl β-ethylamino-acrylate in 50 ml of absolute pyridine are initially introduced, and 0.1 mol of pentachlorophenylsulphenyl chloride is added in portions. Thereafter, the mixture is heated for a further 15 minutes at 60° C., and the pyridine is then stripped in vacuo. The residue is taken up in dichloromethane and water; the organic phase is separated off, washed several times with water and then evaporated down. The residue is recrystallised from acetone.

M.p.: 135° C.

Yield: 53% of theory.

The following compounds were prepared analogously:

| Example No. | Formula | M.p. [°C.] | Yield [% of theory] |
|---|---|---|---|
| 2 | | 97–101 | 48 |
| 3 | | 94–97 | 86 |
| 4 | | 186–189 | 66 |
| 5 | | 83–84 | 68 |

EXAMPLE 6

Preparation of methyl α-[(2,4-dichloro-5-nitrophenyl)-sulphinyl]-β-ethylamine-acrylate

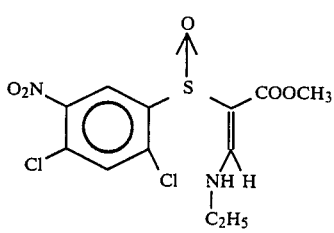

0.01 mol of methyl α-[(2,4-dichloro-5-nitrophenyl)-sulphenyl]-β-ethylamino acrylate in 100 ml of dichloromethane are initially introduced, and 0.01 mol (or 0.02 mol for the sulphone) of m-chloroperbenzoic acid is added in portions at room temperature. After 48 hours at room temperature, the mixture is neutralised with bicarbonate solution, and the organic phase is separated off and evaporated down. The residue is recrystallised with ether.

M.p.: 140°–143° C.

Yield: 92% of theory.

The following compounds were prepared analogously:

| Example No. | Formula | M.p. [°C.] | Yield [% of theory] |
|---|---|---|---|
| 7 | | 120–123 | 43 |
| 8 | | 172–174 | 35 |
| 9 | | 193–195 | 76 |
| 10 | | 150–155 | 69 |

EXAMPLE 11

Preparation of 2-methoxycarbonyl-4-ethyl-5,6,7,8-tetrachloro-4H-1,4-benzothiazine-1-oxide

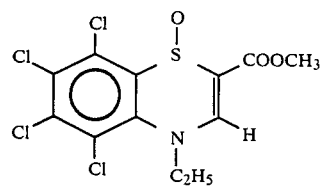

2.13 g (0.005 mol) of methyl α-[(pentachlorophenyl)-sulphinyl]-β-ethylamino-acrylate in 50 ml of absolute dioxane are initially introduced, and 2.3 ml of a 20% strength solution of butyl-lithium in hexane are added at room temperature. After 10 hours at room temperature, the dioxane is stripped off, the residue is taken up in water/dichloromethane and the organic phase is separated off. After the solvent has been stripped off, a viscous oil remains, which can be crystallised with ether.

M.p.: 157°–158° C.,

Yield: 1.23 g (=63% of theory).

EXAMPLE 12

Preparation of 2-methoxycarbonyl-4-ethyl-7-nitro-4H-1,4-benzothiazine

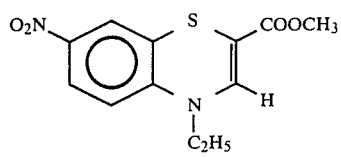

0.01 mol of methyl α-[(5-nitro-phenyl)-sulphenyl]-β-ethylamino-acrylate in 50 ml of absolute dimethylsulphoxide are initially introduced, and 0.01 mol of freshly sublimed potassium tert.-butylate is added in portions at room temperature. After 8 hours at 100° C., the dimethylsulphoxide is stripped off, the residue is taken up in water/dichloromethane and the organic phase is separated off. After the solution has been evaporated down, the residue is crystallised with ether.

M.p.: 162°–166° C.,

Yield: 90% of theory.

The following compounds were prepared analogously:

| Example No. | formula | M.p. [°C.] | Yield [% of theory] |
|---|---|---|---|
| 13 | (structure) | 185–189 | 85 |
| 14 | (structure) | 172–175 | 90 |
| 15 | (structure) | 145 | 15 |
| 16 | (structure) | 163–166 | 76 |
| 17 | (structure) | 157–162 | 85 |
| 18 | (structure) | 178–180 | 47 |
| 19 | (structure) | 188–192 | 70 |
| 20 | (structure) | 140–142 | 38 |

EXAMPLE 21

Preparation of 4-ethyl-5,6,7,8-tetrachloro-4H-1,4-benzothiazine-1-oxide-2-carboxylic acid

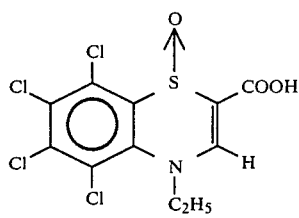

1.95 g (0.005 mol) of the corresponding methyl ester are dissolved in a mixture of 10 ml of dioxane and 10 ml of 6% strength sodium hydroxide solution, and the solution is warmed for 4 hours at 50° C. Thereafter, water and dioxane are stripped off, the residue is taken up in water and the solution is acidified with concentrated hydrochloric acid. The precipitate can be crystallised with ether.

M.p.: 226°–228° C.

Yield: 0.74 g ($\triangleq$40% of theory)

The following compound is obtained analogously:

EXAMPLE 22

4-Ethyl-7-nitro-4H-1,4-benzothiazine-2-carboxylic acid

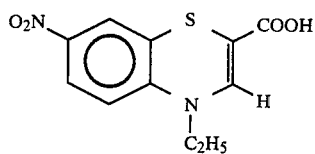

M.p.: 193°–195° C.
Yield: 56% of theory.

We claim:

1. A 4H-1,4-benzothiazine compound of the formula (I)

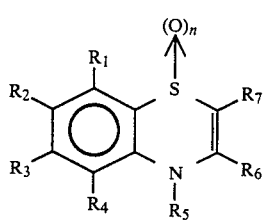

in which
n represents 0, 1, or 2,
$R_1$ and $R_4$ are identical or different and each represent hydrogen or halogen,
$R_2$ and $R_3$ are identical or different and each represent hydrogen, halogen or nitro,
$R_5$ and $R_6$ are identical or different and each is hydrogen or $C_1$–$C_4$-alkyl,
$R_7$ represents $C_1$–$C_4$-alkyl, $C_1$–$C_4$-alkoxycarbonyl or carboxyl
with the proviso that $R_1$, $R_2$, $R_3$ and $R_4$ do not denote hydrogen simultaneously.

2. A 4H-1,4-benzothiazine compound of the formula(I) according to claim 1, in which $R_1$ and $R_4$ simultaneously denote hydrogen.

3. An antibacterial composition for combatting bacterial infections in warm-blooded animals which comprises an anti-bacterially effective amount of a compound of claim 1 together with an inert pharmaceutical carrier.

4. An antibacterial composition of claim 3 in the form of a sterile or physiologically isotonic aqueous solution.

5. An antibacterial according to claim 3 containing from 0.5 to 95% of the said active ingredient, by weight.

6. A medicament in dosage unit form comprising an amount effective for treating bacterial infections of a compound as defined in claim 1 either alone or in admixture with a diluent.

7. A medicament in claim 6 in the form of tablets, pills, dragees, capsules, ampoules, or suppositories.

8. A method of combating bacterial infections in warm-blooded animals which comprises administering to the animals a compound effective for treating bacterial infection as defined in claim 1 either alone or in admixture with a diluent or in the form of a medicament.

9. A method according to claim 8 in which the active compound is administered orally in an amount of 5 to 1000 mg per kg body weight per day.

10. A method according to claim 9 in which the active compound is administered orally in an amount of 10 to 200 mg/kg of body weight per day.

* * * * *

UNITED STATES PATENT AND TRADEMARK OFFICE
CERTIFICATE OF CORRECTION

PATENT NO. : 4,548,934
DATED : October 22, 1985
INVENTOR(S) : Gerd Fengler, et al.

It is certified that error appears in the above-identified patent and that said Letters Patent is hereby corrected as shown below:

| | |
|---|---|
| Col. 3, line 45 | Insert --(b)-- next to formula |
| Col. 3, line 60 | Insert --(c)--next to formula |
| Col. 4, line 10 and Col. 13, line 15 | Correct spelling of "carbocyclic" |
| Col. 4, line 11 | Insert --(d)-- next to formula |
| Col. 4, line 22 | Insert --(e)-- next to formula |
| Col. 4, line 39 | Delete "in" second instance |
| Col. 6, line 56 | Delete "v" and substitute --V-- |
| Col. 8, line 38 | Delete "N" and substitute --n-- |
| Col. 8, line 59 | Correct spelling of "well" |
| Col. 9, line 51 | Delete "bacterial" and substitute --bacteria-- |
| Col. 12, lines 44-47 | In four instances delete " $\leqq$ " and substitute -- $\leq$ -- |
| Col. 15, line 27 | Delete "of" and substitute --or-- |
| Col. 19, line 5 | Delete "=" before "63%" and substitute -- $\widehat{=}$ -- |
| Col. 22, line 15 | After "antibacterial" insert --composition-- |

Signed and Sealed this

Twenty-fifth Day of February 1986

[SEAL]

Attest:

DONALD J. QUIGG

Attesting Officer  Commissioner of Patents and Trademarks